US00PP20795P2

(12) United States Plant Patent
Fleischle

(10) Patent No.: US PP20,795 P2
(45) Date of Patent: Mar. 2, 2010

(54) ***STREPTOCARPUS* PLANT NAMED 'SPIRIT'**

(50) Latin Name: *Streptocarpus×hybridus Voss*
Varietal Denomination: Spirit

(75) Inventor: Achim Fleischle, Vaihingen/Enz (DE)

(73) Assignee: Fleischle Gartenbau GbR, Vaihingen/Enz (DE)

( * ) Notice: Subject to any disclaimer, the term of this patent is extended or adjusted under 35 U.S.C. 154(b) by 0 days.

(21) Appl. No.: 12/150,575

(22) Filed: Apr. 29, 2008

(51) Int. Cl.
*A01H 5/00* (2006.01)

(52) U.S. Cl. ..... Plt./333

(58) Field of Classification Search ..... Plt./333
See application file for complete search history.

*Primary Examiner*—June Hwu
(74) *Attorney, Agent, or Firm*—Mark P. Bourgeois

(57) ABSTRACT

A new cultivar of *Streptocarpus* plant named 'Spirit' that is characterized by a large quantity of violet-blue flowers with a darker purple center venation.

1 Drawing Sheet

Botanical classification: *Streptocarpus×hybridus* Voss.
Variety denomination: 'Spirit'.

BACKGROUND OF THE INVENTION

The present invention relates to a new and distinct cultivar of *Streptocarpus* plant botanically known as *Streptocarpus* and hereinafter referred to by the cultivar name 'Spirit'.

'Spirit' was discovered by the inventor in March of 2005 in Vaihingen/Enz, Germany. 'Spirit' was discovered as a naturally occurring whole plant mutation in a bed of *Streptocarpus* 'Targa' (not patented) within a glass greenhouse.

Asexual reproduction of the new cultivar 'Spirit' first occurred by leaf cuttings in July of 2005 in Vaihingen/Enz, Germany. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Streptocarpus* cultivar 'Spirit'. These traits in combination distinguish 'Spirit' as a new and distinct cultivar apart from other existing known varieties of *Streptocarpus*.

1. *Streptocarpus* 'Spirit' exhibits a large quantity of flowers.
2. *Streptocarpus* 'Spirit' exhibits violet-blue flowers with a darker purple center venation.

The closest comparison cultivar is the parent plant *Streptocarpus* 'Targa' 'Spirit' is distinguishable from 'Targa' by the following characteristics:

1. 'Spirit' has violet-blue flowers with a darker purple center venation. The veins on the upper two petals are lighter. The flowers of 'Targa' are dark violet-purple with a lighter margin on the lower petals.
2. 'Spirit' has purple-green pedicels. The pedicels of 'Targa' are darker.

BRIEF DESCRIPTION OF THE DRAWING

The accompanying photograph illustrates the distinguishing traits of *Streptocarpus* 'Spirit'. The plant in the photograph shows an overall view of a 10 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Streptocarpus* cultivar named 'Spirit'. Data was collected in Vaihingen/Enz, Germany from 10 week old glass greenhouse grown plants in 12 cm. diameter containers. The time of year was Winter and the temperature range was 20–22 degrees Centigrade during the day and 18–22 degrees Centigrade at night. The light level was 2000 to 3000 Lux. No photoperiodic treatments or growth retardants were used. Color determinations are in accordance with The Royal Horticultural Society Colour Chart 2007 edition, except where general color terms of ordinary dictionary significance are used. The growing requirements are similar to the species. 'Spirit' has not been tested under all possible conditions and phenotypic differences may be observed with variations in environmental, climatic, and cultural conditions, however, without any variance in genotype.

Botanical classification: *Streptocarpus* 'Spirit'.
Use: Indoor plant or ornamental perennial in warmer climates.
Parentage: 'Spirit' is a naturally occurring whole plant mutation of *Streptocarpus* 'Targa'.
Vigor: Moderate.
Growth habit: Ground hugging, clump forming.
Plant shape: Rounded, clump forming plant with upright leaves.
Suitable container size: 12 cm. pots.
Height: 19 cm. in height.
Width: 34 cm. in width.
Low temperature tolerance: 8° Centigrade.
High temperature tolerance: 30° Centigrade.
Propagation: Leaf cuttings.
Time to initiate roots in summer: 25 days to initiate roots at 24° Centigrade.
Time to initiate roots in winter: 21 days to initiate roots at 22° Centigrade.
Time to produce a rooted cutting or liner in summer: 135 days at 24° Centigrade.
Time to produce a rooted cutting or liner in winter: 125 days at 22° Centigrade.

Crop time: Approximately 8 to 10 weeks.
Root system: Fibrous.
Stem: No stems, Leaves grow directly from base, Average 12 clumps.
Foliage:
*Texture.*—Dull.
*Leaf arrangement.*—In whorls.
*Compound or single.*—Single.
*Leaf shape.*—Obolanceolate.
*Leaf apex.*—Obtuse.
*Leaf base.*—Attenuate.
*Leaf length.*—21.0 cm. in length.
*Leaf width.*—6.0 cm. in width.
*Pubescence.*—Upper side coarse and dense, lower side puberulent.
*Leaf margin.*—Crenulate, undulate.
*Young leaf color* (*lower surface*).—139D.
*Young leaf color* (*upper surface*).—137A.
*Mature leaf color* (*lower surface*).—139D.
*Mature leaf color* (*upper surface*).—137A.
*Vein color* (*under surface*).—199B to 147D.
*Vein color* (*upper surface*).—147B.
*Venation pattern.*—Strong midrib with alternating lateral veins.
*Leaf attachment.*—Petiolate.
*Petiole dimensions.*—2 cm. in length, and 70 mm. in diameter.
*Petiole surface texture.*—Sparse pubescent.
*Petiole color.*—199A.
Flower:
*Inflorescence arrangement.*—Raceme.
*Flowering habit.*—Continuous.
*Quantity of flowers per inflorescence.*—2 to 3.
*Inflorescence dimensions.*—18 cm. in height and 10 cm. in width.
*Flower type.*—Zygomorph with five petals fused to a conical throat ending in a flaring five lobed corolla disk.
*Quantity of flowers per lateral stem.*—2–3.
*Quantity of flower buds per lateral stem.*—2–3.
*Quantity of flowers and buds per plant.*—At any given time up to 20.
*Natural flowering season.*—All year.
*Fragrance.*—None.
*Rate of flower opening.*—Within two weeks of visible raceme.
*Flower bud length.*—4 cm.
*Flower bud diameter.*—1.5 cm.
*Flower bud shape.*—Elongated, club-shaped.
*Bud color.*—*N*87A.
*Rate of bud opening.*—2 days.
*Flower aspect.*—Funnel drooping, corolla disk outward-facing.
*Flower shape.*—Trumpet-shaped with flat, flaring corolla disk.
*Flower dimensions.*—5 cm. in diameter and 5 cm. in depth.
*Flower longevity.*—4–5 days.
*Petal texture.*—Velvety, soft.
*Number of petals.*—5.
*Fused or unfused.*—Fused.
*Petal arrangement.*—Evenly spaced, radiating, zygomorphic.
*Petal shape.*—Orbicular.
*Petal margin.*—Crenate.
*Petal apex.*—Obtuse.
*Petal length.*—14–16 mm. before fused to corolla.
*Petal width.*—2.25 cm.
*Petal color when opening* (*upper side*).—N88B, three lower petals have center venation 89A, two upper petals have center venation N89D.
*Petal color when opening* (*under side*).—88B to 88C.
*Petal color fully opened* (*upper side*).—N88B, three lower petals have center venation 89A, two upper petals have center venation N89D.
*Petal color fully opened* (*under side*).—88B to 88C.
*Petal color fading to.*—Not fading.
*Throat.*—Tubular, 29 mm. in length, 6 mm. in diameter near base, 9 mm. in diameter at flare, inner color N88D, outer color N88C.
*Self-cleaning or persistent.*—Self-cleaning.
Sepals:
*Number of sepals.*—5.
*Sepal shape.*—Linear.
*Sepal margin.*—Entire.
*Sepal apex.*—Acuminate.
*Sepal base.*—Fused, linear.
*Sepal dimensions.*—5 mm. in length and 2 mm. in width.
*Young sepal color* (*upper side*).—139A.
*Young sepal color* (*under side*).—139A.
*Mature sepal color* (*upper side*).—139A.
*Mature sepal color* (*under side*).—139A.
Calyx:
*Calyx shape.*—Elongated corona.
*Calyx dimensions.*—7 mm. in length and 3 mm. in diameter.
Peduncle:
*Peduncle length.*—0.5 cm.
*Peduncle diameter.*—2 mm.
*Peduncle strength.*—Moderate.
*Peduncle surface texture.*—Sparse pubescent.
*Peduncle color.*—N89A.
Pedicels:
*Pedicel length.*—17 cm.
*Pedicel diameter.*—3 mm.
*Pedicel strength.*—Strong.
*Pedicel surface texture.*—Sparse pubescent.
*Pedicel color.*—N199A.
Reproduction organs:
*Stamen number.*—Two.
*Anther shape.*—Fused.
*Anther color.*—162B.
*Amount of pollen.*—Low.
*Pollen color.*—162B.
*Pistil number.*—One.
*Pistil length.*—3 cm. in length.
*Stigma shape.*—Deltoid, bifurcate.
*Stigma color.*—85C.
*Style length.*—12 mm.
*Style color.*—85C.
*Ovary color.*—N199A.
Fruit:
*Fruit dimensions.*—2.5 cm. in length and 0.5 cm. in diameter.
*Fruit color.*—165A.
Seed:
*Seed dimensions.*—0.3 mm. in length and 0.2 mm. in diameter.
*Seed color.*—165D.
*Quantity of seeds.*—50–60.
Disease resistance: Susceptible to *Streptocarpus* flower mottle virus.

The invention claimed is:

1. A new and distinct variety of *Streptocarpus* plant named 'Spirit' as described and illustrated.

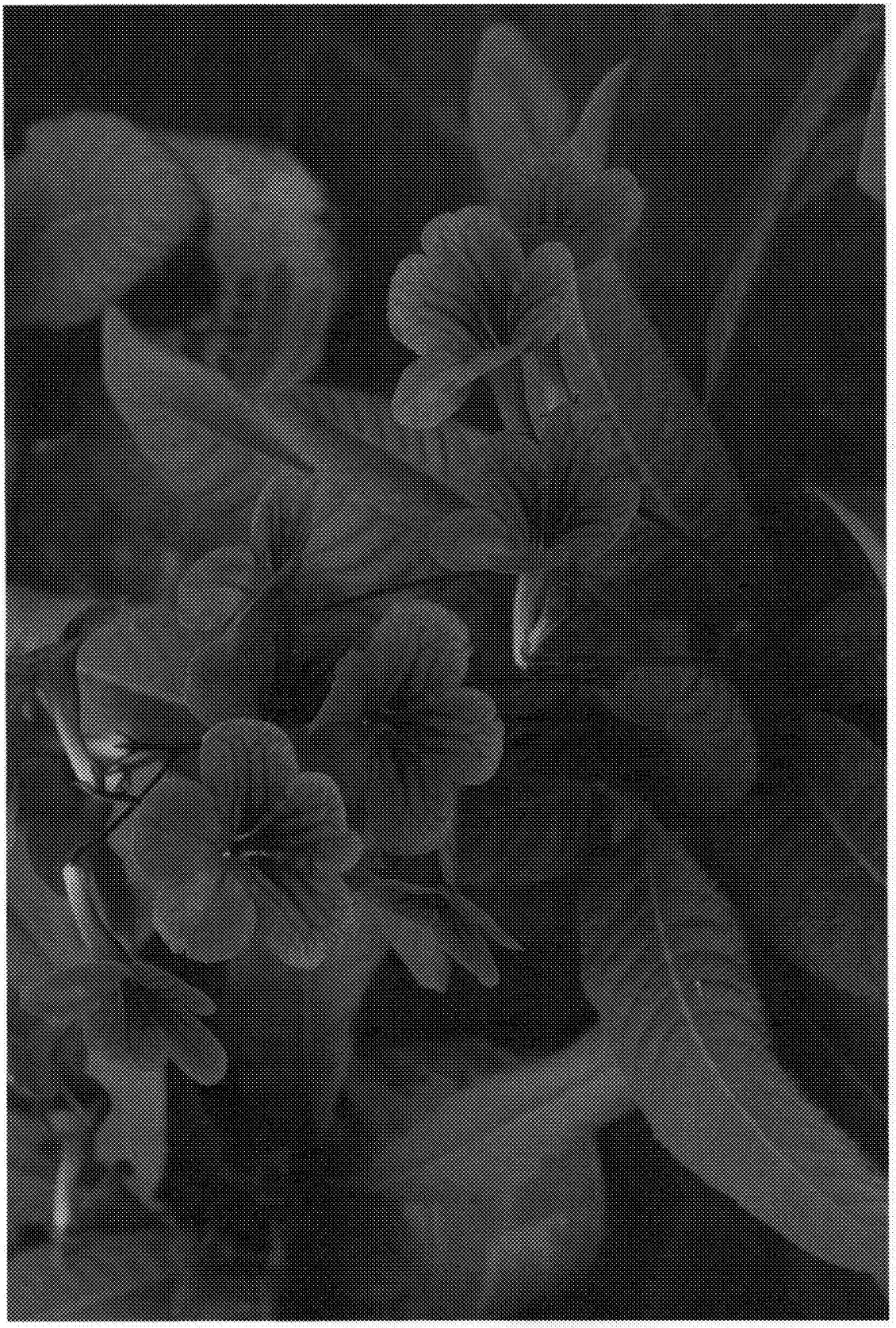

* * * * *